(12) United States Patent
Olsen et al.

(10) Patent No.: US 10,646,609 B2
(45) Date of Patent: May 12, 2020

(54) ACTIVITY-BASED TARGETED DISINFECTION SYSTEM

(71) Applicants: Joseph Olsen, Gloucester, MA (US); Michael A. Quilici, Essex, MA (US)

(72) Inventors: Joseph Olsen, Gloucester, MA (US); Michael A. Quilici, Essex, MA (US)

(73) Assignee: OSRAM SYLVANIA Inc., Wilmington, MA (US)

( * ) Notice: Subject to any disclaimer, the term of this patent is extended or adjusted under 35 U.S.C. 154(b) by 260 days.

(21) Appl. No.: 15/789,083

(22) Filed: Oct. 20, 2017

(65) Prior Publication Data

US 2019/0117812 A1  Apr. 25, 2019

(51) Int. Cl.
| | |
|---|---|
| *A61L 2/26* | (2006.01) |
| *G16H 40/20* | (2018.01) |
| *G16H 40/63* | (2018.01) |
| *A61L 2/10* | (2006.01) |
| *A61L 2/18* | (2006.01) |

(52) U.S. Cl.
CPC ............... *A61L 2/26* (2013.01); *G16H 40/20* (2018.01); *G16H 40/63* (2018.01); *A61L 2/10* (2013.01); *A61L 2/18* (2013.01); *A61L 2202/14* (2013.01); *A61L 2202/16* (2013.01); *A61L 2202/25* (2013.01)

(58) Field of Classification Search
CPC ..... A61L 2/26; A61L 2/18; A61L 2/10; A61L 2202/25; A61L 2202/16; A61L 2202/14; G16H 40/20
See application file for complete search history.

(56) References Cited

U.S. PATENT DOCUMENTS

2017/0076042 A1* 3/2017 Katz .................... G08B 21/245

FOREIGN PATENT DOCUMENTS

| WO | 2011010233 A2 | 1/2011 |
| WO | 2015087331 A1 | 6/2015 |
| WO | 2015116876 A1 | 8/2015 |

OTHER PUBLICATIONS

Kleiminger, Lisa, International Search Report and Written Opinion of the International Searching Authority, for counterpart application PCT/US2018/054974, dated Jan. 30, 2019, European Patent Office, Rijswijk, The Netherlands, 15 pages.

* cited by examiner

*Primary Examiner* — Toan M Le
(74) *Attorney, Agent, or Firm* — Yutian Ling

(57) ABSTRACT

Various implementations disclosed herein include a method for aiding disinfection of a room. The method may include collecting, by one or more sensors in a disinfection system, activity data in the room. A computing device or output device may identify one or more hot spots from the activity data, in which the one or more hot spots indicate areas in the room for cleaning, and generate a contamination map containing the one or more hot spots. The output device may output the contamination map to an output device for viewing by a user.

15 Claims, 6 Drawing Sheets

ACTIVITY-BASED TARGETED DISINFECTION SYSTEM

FIELD OF THE DISCLOSURE

This disclosure relates to disinfection systems, and more specifically to a sensor-based disinfection system for tracking activity data in a room and using the data to assist personnel cleaning the room.

BACKGROUND

Some human environments require constant and thorough cleaning as part of its use. One common example are hospital rooms (e.g., exam rooms and surgical rooms), which are disinfected after every use to kill any remaining harmful bacteria and viruses in order to prevent the spread of infection and disease. Cleaning staff work quickly to prepare each room for the next patient. However, cleaning staff must also clean each room thoroughly, which may be difficult if the hospital is facing short turn-around times between patients. In addition, cleaning staff also do not witness the prior activity in the room, and so may not know which surfaces, areas, and objects were used. Therefore, the cleaning staff tends to clean most if not all parts of the room.

SUMMARY

Various implementations disclosed herein may include a disinfection system. The disinfection system may include one or more sensors configured to collect activity data in a room, and output the activity data. The disinfection system may further include an output device configured to receive the activity data from the one or more sensors, identify one or more hot spots based on the activity data, in which the one or more hot spots indicate areas in the room for cleaning, generate a contamination map containing the one or more hot spots, and display the contamination map to a user.

In some embodiments, the one or more sensors are further configured to collect cleaning activity data in the room, and output the cleaning activity data, and the output device is further configured to update the contamination map based on the cleaning activity data, and display the updated contamination map to the user. In some embodiments, the cleaning activity data may include at least one of radiance measurements of the one or more hot spots during cleaning and an amount of time a disinfectant has been applied to the one or more hot spots. In some embodiments, the one or more sensors may include at least one of an infrared sensor, a depth-sensing camera, a laser scanner, a three dimensional motion sensor, a two dimensional motion sensors, an ultraviolet sensor, a thermal imager, and a time-of-flight depth sensor. In some embodiments, the output device may include one of an augmented reality system, a mobile computing device, and a projector. In some embodiments, the activity data may include at least one of a location and size of a person's contact with a surface in the room, an amount of time a person has contacted the surface, movement of objects within the room, movement of liquids in the room, and changes in properties of objects and surfaces in the room.

Further implementations disclosed herein may include a disinfection system. The disinfection system may include one or more sensors configured to collect activity data in a room, and output the activity data. The disinfection system may further include a computing device configured to receive the activity data from the one or more sensors, identify one or more hot spots based on the activity data, in which the one or more hot spots indicate areas in the room for cleaning, generate a contamination map containing the one or more hot spots, and output the contamination map to a output device. The disinfection system may further include the output device, which is configured to display the contamination map to a user.

In some embodiments, the one or more sensors are further configured to collect cleaning activity data in the room and output the cleaning activity data, the computing device is further configured to receive the cleaning activity data, update the contamination map based on the cleaning activity data, and output the updated contamination map to the output device, and the output device is further configured to display the updated contamination map to the user. In some embodiments, the cleaning activity data may include at least one of radiance measurements of the one or more hot spots during cleaning and an amount of time a disinfectant has been applied to the one or more hot spots. In some embodiments, the one or more sensors may include at least one of an infrared sensor, a depth-sensing camera, a laser scanner, a three dimensional motion sensor, a two dimensional motion sensors, an ultraviolet sensor, a thermal imager, and a time-of-flight depth sensor. In some embodiments, the output device may include one of an augmented reality system, a mobile computing device, and a projector. In some embodiments, the activity data may include at least one of a location and size of a person's contact with a surface in the room, an amount of time a person has contacted the surface, movement of objects within the room, movement of liquids in the room, and changes in properties of objects and surfaces in the room.

Further implementations disclosed herein may include a method for aiding disinfection of a room. The method may include collecting, by one or more sensors, activity data in the room, identifying one or more hot spots from the activity data, in which the one or more hot spots indicate areas in the room for cleaning, generating a contamination map containing the one or more hot spots, and outputting the contamination map to an output device for viewing by a user.

In some embodiments, the method may further include collecting, by the one or more sensors, cleaning activity data in the room as it is cleaned, and updating the contamination map based on the cleaning activity data. In some embodiments, the cleaning activity data may include at least one of radiance measurements of the one or more hot spots during cleaning and an amount of time a disinfectant has been applied to the one or more hot spots. In some embodiments, the one or more sensors may include at least one of an infrared sensor, a depth-sensing camera, a laser scanner, a three dimensional motion sensor, a two dimensional motion sensors, an ultraviolet sensor, a thermal imager, and a time-of-flight depth sensor. In some embodiments, the output device may include one of an augmented reality system, a mobile computing device, and a projector. In some embodiments, the activity data may include at least one of a location and size of a person's contact with a surface in the room, an amount of time a person has contacted the surface, movement of objects within the room, movement of liquids in the room, and changes in properties of objects and surfaces in the room.

The features and advantages described herein are not all-inclusive and, in particular, many additional features and advantages will be apparent to one of ordinary skill in the art in view of the drawings, specification, and claims. Moreover, it should be noted that the language used in the

Figure 1:
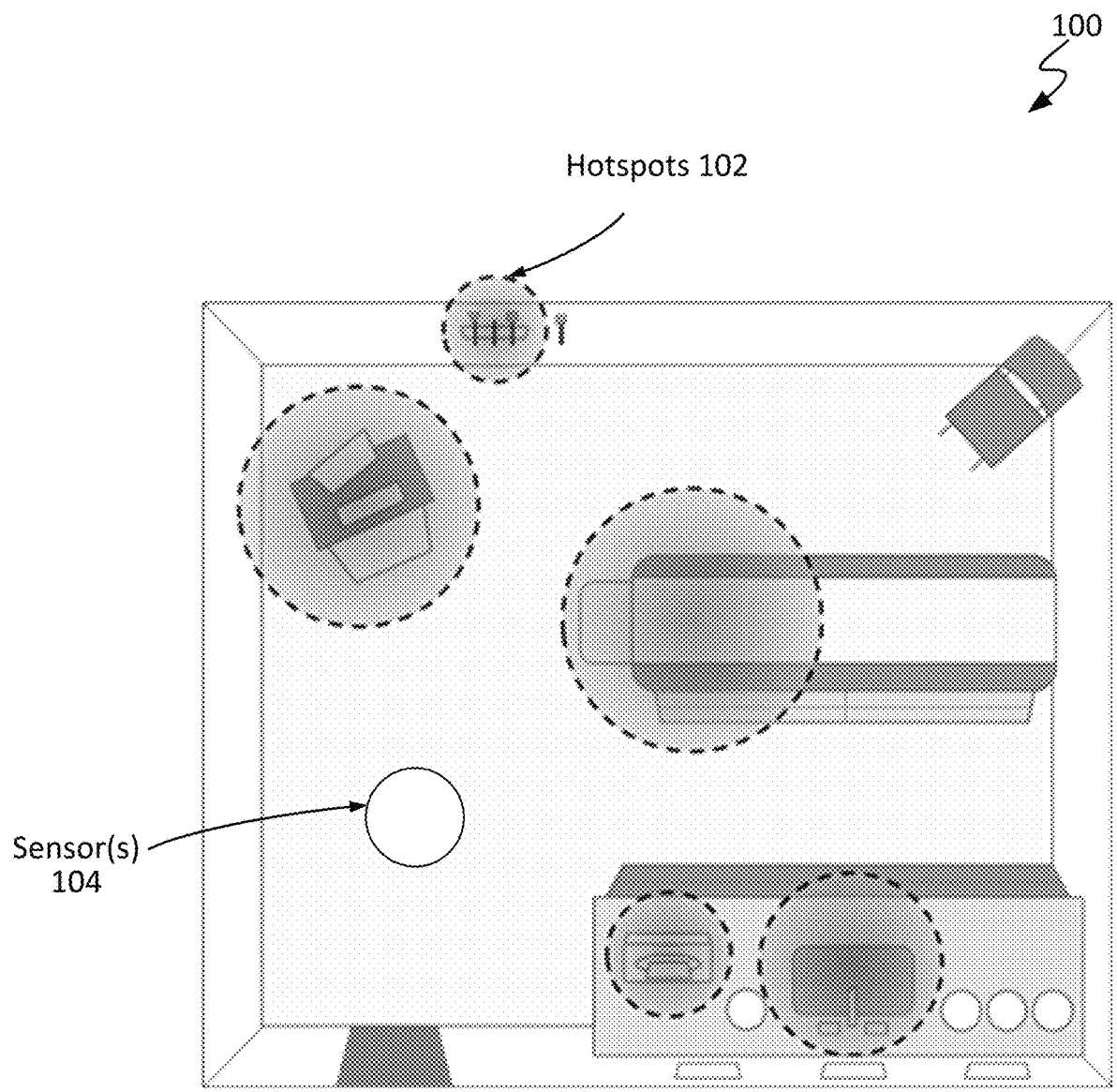
FIG. 1 illustrates a block diagram of a room overlaid with a contamination map in accordance with embodiments of the present disclosure.

These and other features of the present embodiments will be understood better by reading the following detailed description, taken together with the FIG.s herein described. The accompanying drawings are not intended to be drawn to scale. For purposes of clarity, not every component may be labeled in every drawing.

DETAILED DESCRIPTION

Techniques and architecture are disclosed for a disinfection system. The system includes one or more sensors that collect activity data in a room. The activity data may include the movement of people and objects in the room, and physical contact between people and surfaces or objects in the room. The activity data is then sent to a computing device (e.g., a server) or an output device, where a contamination map is generated from the activity data. The contamination map includes one or more hot spots that indicate areas in the room for cleaning (e.g., surfaces which were touched by a person). The output device displays the contamination map to a user, who may be responsible for cleaning the room. With the contamination map, the user may determine which areas of the room should be prioritized for cleaning. As the user cleans the room, the sensors may collect cleaning activity data and the contamination map may be updated. Thus the contamination map may provide real-time feedback to the user about when hot spots are sufficiently cleaned.

General Overview

As discussed above, certain environments such as hospital rooms are cleaned thoroughly and frequently in order to be safe for use. Cleaning staff have opposing goals when cleaning such rooms—the cleaning should be thorough, but also should be completed quickly. Thus cleaning staff are under a lot of pressure to satisfy both goals, and may not always sufficiently clean each room. For example, cleaning staff may not know which surfaces and objects were touched or used, and therefore they may miss potentially contaminated locations, leaving behind bacteria and viruses that can be transmitted to future patients and staff.

Certain technologies have been developed to automate the cleaning process. For example, an ultraviolet (UV)-based disinfection system, such as low pressure mercury lamps, may be installed in a room. The system may emit UV light of certain wavelengths known to kill bacteria and viruses. However, UV-based disinfection systems have inherent safety concerns, especially when operated in the vicinity of humans. In addition, many of these systems flood large areas with UV light from a fixed location and, due to line-of-sight obstructions, may not be effective at disinfecting all surfaces. These systems often broadly disinfect the space without regard to the specific surfaces that actually require disinfection. Thus there is need for safer, more accurate disinfection systems that can identify areas in the room that should be prioritized for cleaning.

Thus, and in accordance with an embodiment of the present disclosure, techniques and architecture are disclosed for a disinfection system. The system includes one or more sensors that collect activity data in a room. The sensors may include an infrared sensor, a depth-sensing camera, a laser scanner, a three dimensional motion sensor, a two dimensional motion sensors, an ultraviolet sensor, a thermal imager, and a time-of-flight depth sensor. The activity data may include the movement of people and objects in the room, physical contact between people and surfaces or objects in the room, and the spread of liquids in the room. The activity data is then sent to a computing device (e.g., a server) or an output device, where a contamination map is generated from the activity data. The contamination map includes one or more hot spots that indicate areas in the room for cleaning (e.g., surfaces which were touched by a person). The computing device (if part of the system) sends the contamination map to the output device. The output device may be, for example, an augmented reality system, a mobile computing device, or a projector. The output device displays the contamination map to a user, who may be responsible for cleaning the room. With the contamination map, the user may determine which areas of the room should be prioritized for cleaning. As the user cleans the room, the sensors may collect cleaning activity data and the contamination map may be updated.

Some advantages of utilizing the above-described system include greater reduction in pathogens, reduced time for disinfection, and improved coverage of surfaces. For example, the system may help aid cleaning staff to identify high priority areas and surfaces to clean, to provide real-time feedback on cleaning progress, and to increase the overall efficiency of the cleaning process. Another advantage of such a system is that it can monitor indirect transfer of pathogens to secondary surfaces. For example a sick patient may touch an object and then, when the object is moved to another surface, the pathogens are transferred to that surface as well. The spread of pathogens quickly becomes dauntingly difficult to track as multiple surfaces become contaminated. A disinfection system that includes object detection and tracking can record all of these transfers and use this information to more effectively disinfect the space.

Disinfection System

FIG. 1 is a block diagram illustrating a room 100 overlaid with a contamination map in accordance with embodiments of the present disclosure. The room 100 may be any room that is regularly and/or thoroughly cleaned, such as hospital rooms (e.g., exam rooms, surgical rooms), hotel rooms, veterinary rooms, and clean rooms. For the purposes of illustration only in the written description, the room 100 may be considered a hospital room. The room 100 may contain a number of objects and surfaces that people in the room may interact with. For example, there may be beds that a patient may lay on, medical equipment, and tables and trays upon which medical equipment are placed.

When the room 100 is in use by one or more persons, those persons may interact with various objects, surfaces, and areas in the room. The activity of people in the room may be tracked using one or more sensors 104. The sensors 104 may include, but are not limited to, an infrared sensor, a depth-sensing camera, a laser scanner, a three dimensional motion sensor, a two dimensional motion sensors, an ultraviolet sensor, a thermal imager, and a time-of-flight depth sensor. The activity that may be tracked by the sensors 104 may include a person touching surfaces or objects, moving objects, sneezes/coughs and the spread of liquids.

Figure 2:
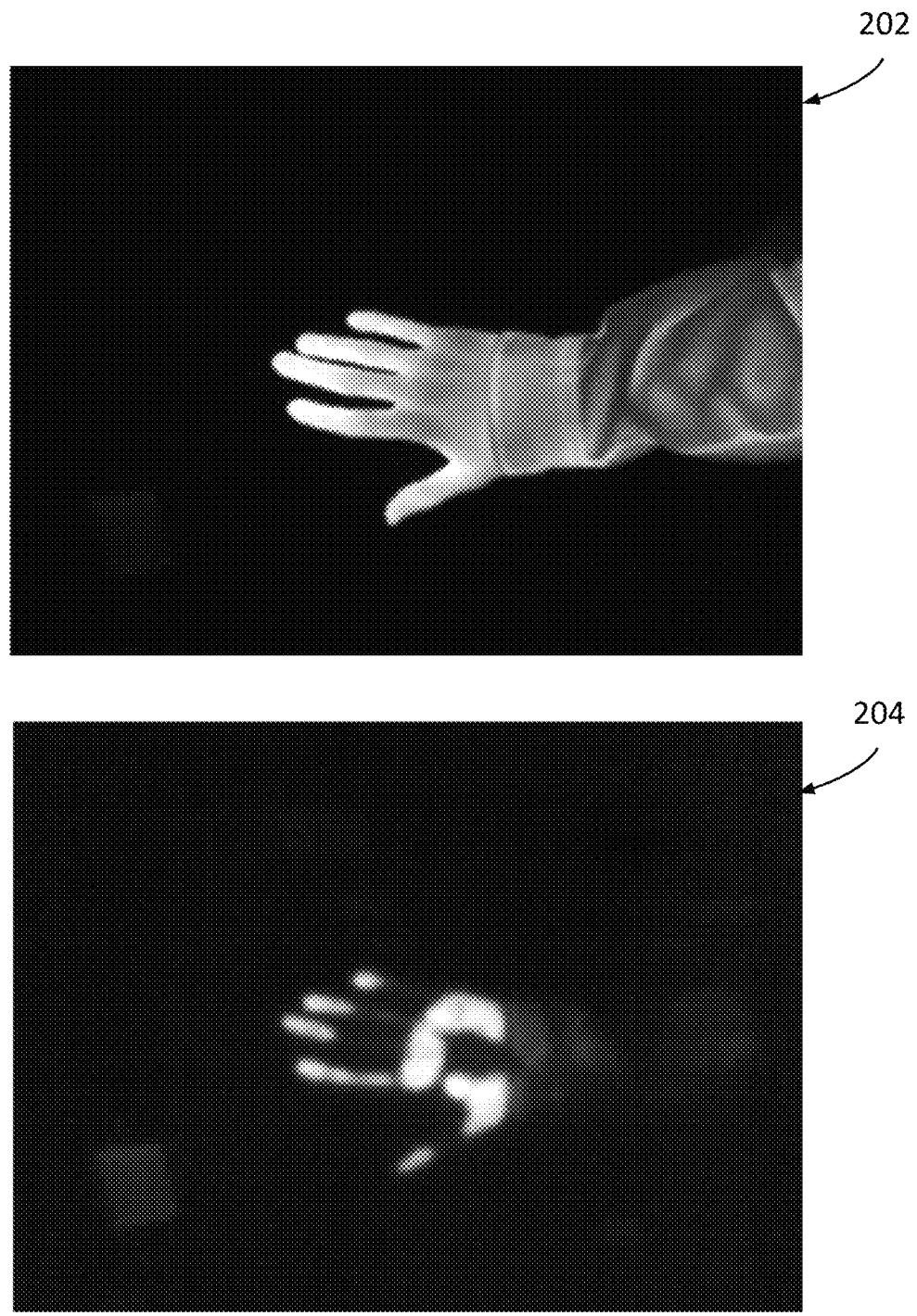
FIG. 2 are images illustrating the detection of human contact with a surface in accordance with embodiments of the present disclosure.

The activity data may include a location and size of a person's contact with a surface in the room, an amount of time a person has contacted the surface, movement of objects within the room, movement of liquids in the room, changes in properties of objects and surfaces in the room, and other parameters. For example, FIG. 2 includes a thermal image 202 of a person touching a surface with his or her hand, and a thermal image 204 after the hand has been removed. As can be seen, the thermal image 204 contains a residual heat signature of the hand contact on the surface. One or more sensors 104, such as a thermal image or infrared sensor, may collect the residual heat signature, its location and size, and the duration of contact as activity data. In another example, 3D sensors may be utilized for accurate 3D positioning of joints and fingers and thus may be used to track the movement of objects in the environment. In another example, flow meters and computational fluid dynamics simulations may be used to determine likely paths from sneezes and other fluid spreads.

The activity data from the sensors 104 may be transmitted to a computing device, such as a server, a central controller, a mobile computing device, or an output device (described with reference to FIG. 3). The computing device/output device may correlate the activity data with a physical map of the room to generate a contamination map. The contamination map contains one or more hot spots 102 that indicate areas that should be cleaned as shown in FIG. 1. For example, the hot spots 102 may include surfaces, areas, or objects that have been physically touched one or more times by a person, exposed to fluids, or objects that have been moved. In some embodiments, there may be a threshold of activity for an area of the room 100 before it is considered a hot spot. For example, there may be a minimum time that a person may occupy or touch a surface or object before it is considered a hot spot, or there may be a minimum number of contacts between a person and a surface before it is considered a hot spot. The thresholds may be user-configurable, depending on the cleaning specifications or parameters. In some embodiments, the contamination map may be able to differentiate between different types of objects, surfaces, and contaminants based on sensor data, and may signify these differences via different colors or other visual indicators.

Figure 3:
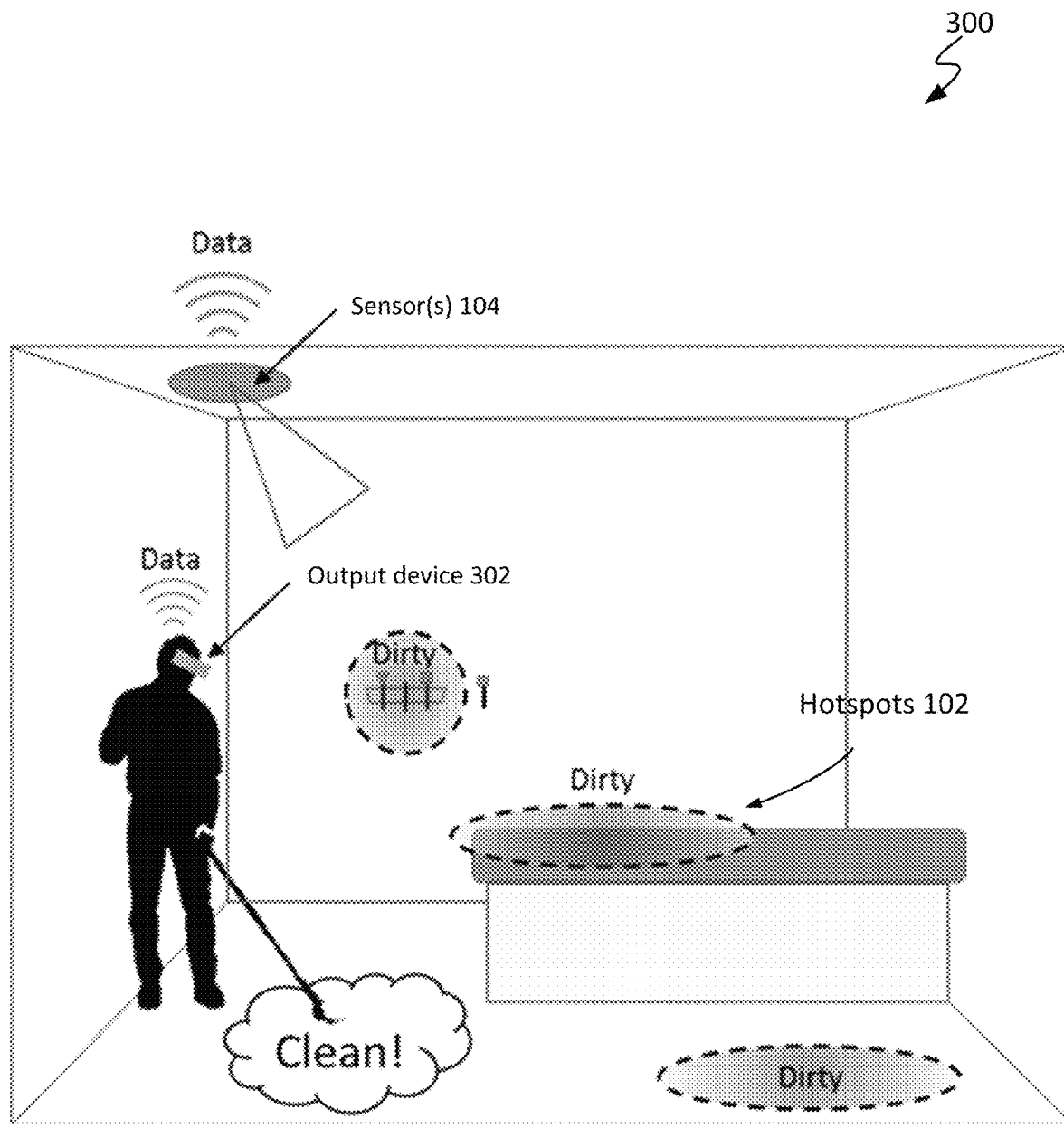
FIG. 3 is a block diagram of a user utilizing a disinfection system in accordance with embodiments of the present disclosure.

The contamination map may be output to a user that is cleaning the room, as illustrated in FIG. 3. FIG. 3 illustrates a block diagram of a user utilizing a disinfection system in a room 300 in accordance with embodiments of the present disclosure. The room 300 may be similar to the room 100, and includes a variety of objects and surfaces that people may interact with. The room 300 includes one or more sensors 104 that collect activity data of people interacting with surfaces and objects in the room 300. The activity data is used to generate a contamination map that includes hot spots 102. The hot spots 102 indicate areas of the room 300 that should be cleaned based on the activity data.

The contamination map may be output to an output device 302 used by a user. The user may be one or more people responsible for cleaning the room 300. The output device 302 may include, but is not limited to, an augmented reality system, a mobile computing device, or a projector. For illustrative purposes only, the output device 302 illustrated in FIG. 3 may be an augmented reality system that overlays the contamination map onto a person's view of the room 300. For example, the output device 302 may include goggles for the user to wear. The goggles may overlay or project a virtual image of the hot spots 102 onto a view of the room 300 that the user sees through the goggles. Thus the output device 302 indicates to the user which areas of the room 300 are considered hot spots 102 that should be cleaned. In another example, the output device 302 may be a mobile computing device, such as a smartphone or tablet, which displays the contamination map to the user. In another example, the output device 302 may be a projector that projects images of the hot spots 102 onto the corresponding areas of the room 300. In general, the output device 302 provides a visualization of the contamination map and the hot spots 102 to the user to aid the user in prioritizing which areas of the room 300 should be cleaned.

Figure 4:
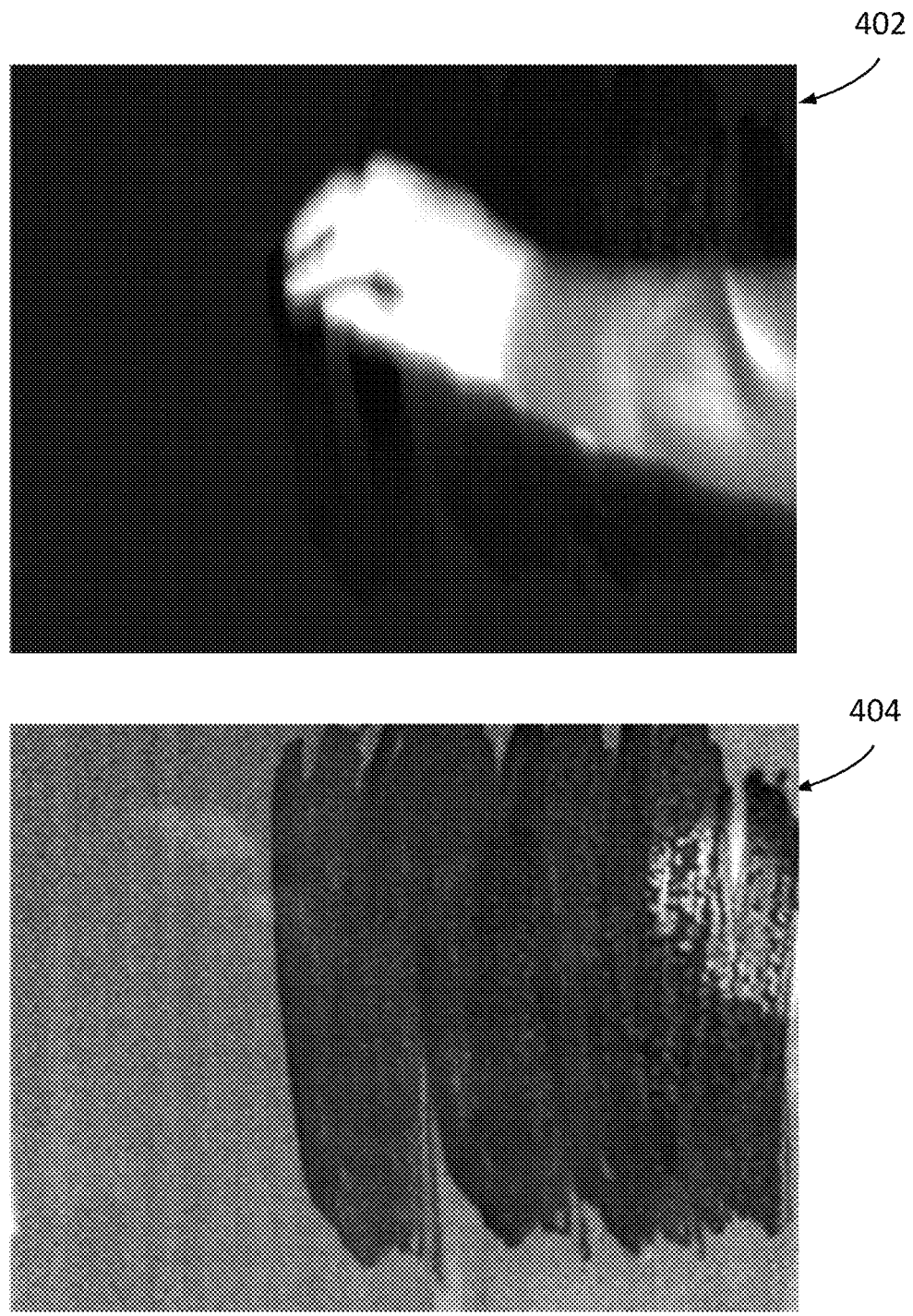
FIG. 4 are images illustrating the detection of cleaning activity in accordance with embodiments of the present disclosure.

The sensors 104 may collect cleaning activity data while the user cleans the room 300. The cleaning activity data may be used to update the contamination map and the hot spots 102 to provide an indication of cleaning progress to the user. For example, FIG. 4 shows a thermal image 402 of a person cleaning a surface with a liquid solution, and a thermal image 404 of the surface after cleaning. The liquid cools the surface due to evaporation, which may be detected by an infrared sensor or other thermal sensor as seen in thermal image 404. Thus the sensors 104 may be able to track which hot spots 102 have been cleaned by the user. The sensors 104 may transmit this data to a computing device or the output device 302, which updates the contamination map as hot spots 102 are cleaned. For example, the hot spots 102 may change to another color to indicate that the hot spot has been cleaned, or may be removed from the contamination map.

In some embodiments, the disinfection system may also track the effectiveness of the cleaning process. For example, there may be a policy or requirement that a cleaning solution should be applied and allowed to set for a minimum amount of time (e.g., 5 minutes) in order to be effective. The sensors 104 and the computing device/output device 302 may track the amount of time that cleaning solutions have remained on a hot spot, and indicate to the user when the prescribed amount of time has elapsed so that the hot spot has been sufficiently cleaned.

In another example, the disinfection system may be able to calculate the level of disinfection using radiance measurements. The level of disinfection may be strongly affected by the dose or "fluence" or "radiant exposure" of the surface or object being cleaned. The dose may be the amount of UV power applied to a surface over a specified time frame. The dose may be measured in units of Joules per square meter ($J/m^2$) and may be calculated as irradiance multiplied by time. Dose is often measured at a single point using a calibrated UV irradiance meter or spectrometer. The challenge with disinfecting large spaces such as hospital rooms is knowing if the proper dose has been applied to all surfaces. Thus in some embodiments, the sensors 104 may include a calibrated UV radiance imager or sensor that can measure the radiance of a surface. The sensor measurements may be combined with knowledge of UV reflectivity for different surfaces to determine the dose of the surface. For example, the computing device/output device 302 may estimate the irradiance of a surface using the radiance measurements collected by the sensors 104. The irradiance may be calculated as $E=L\pi/\rho$, in which E is the irradiance, L is the measured radiance, $\pi$ is the solid angle of a lambertian source (which may vary if the source is more specular), and $\rho$ is the reflectivity of the surface. The computing device/output device 302 may store in memory the reflectivity of each surface in the room. Then, to determine the total dose, H, the computing device/output device 302 may multiply the irradiance by time, $H=E*t$, or if the irradiance varies over time $H=\int E(t)dt$. The computing device/output device 302 may utilize the dose calculations to determine whether a hot spot has been sufficiently cleaned (e.g., the disinfectant has had enough time to set).

Figure 5:
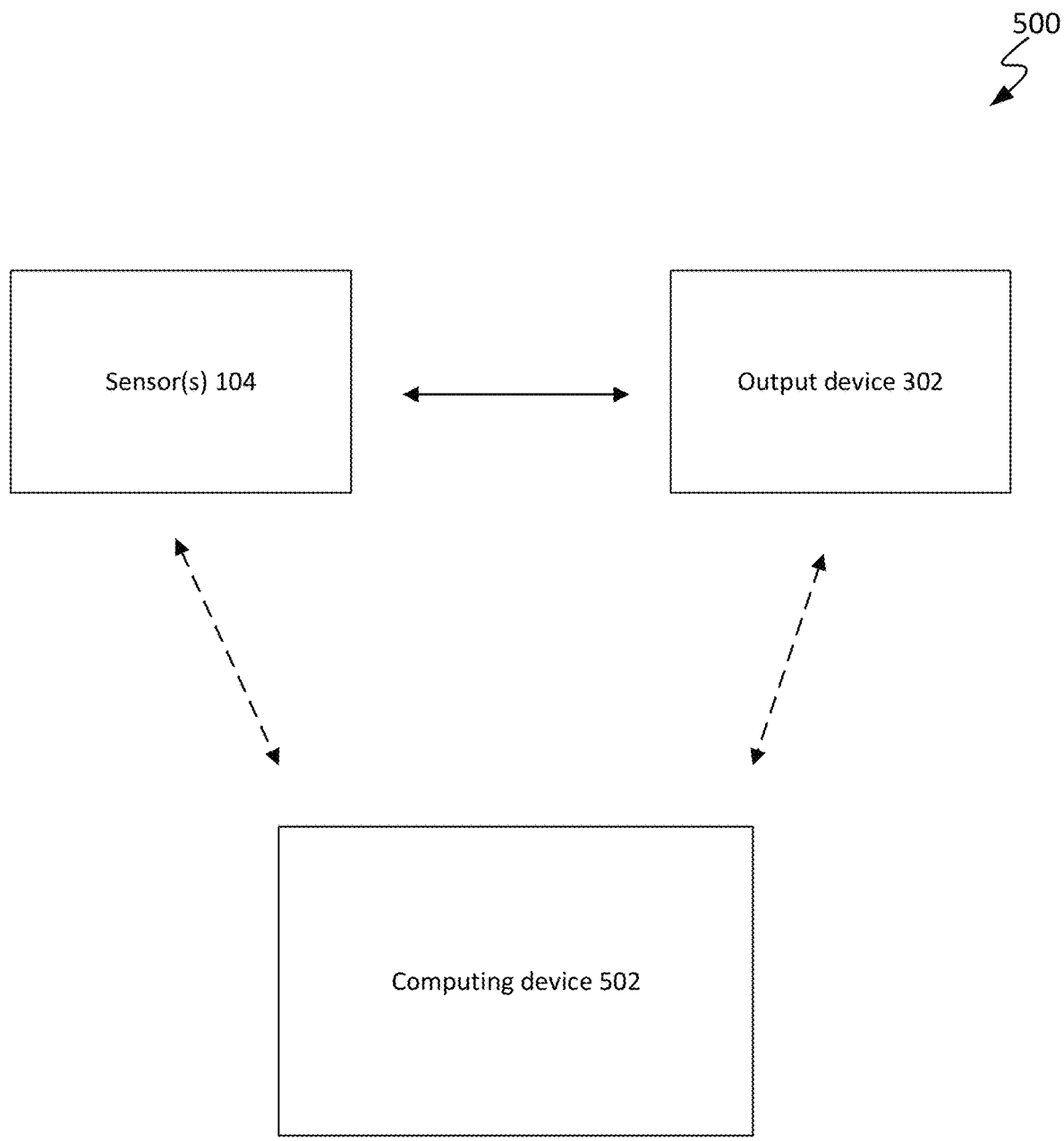
FIG. 5 illustrates a block diagram of a disinfection system in accordance with embodiments of the present disclosure.

FIG. 5 illustrates a block diagram of a disinfection system 500 in accordance with embodiments of the present disclosure. The disinfection system 500 may include sensors 104. The sensors 104 may include, but are not limited to at least one of an infrared sensor, a depth-sensing camera, a laser scanner, a three dimensional motion sensor, a two dimensional motion sensors, an ultraviolet sensor, a thermal imager, and a time-of-flight depth sensor. The sensors 104 may be configured to collect activity data within a room, which is used to generate a contamination map used for cleaning. The sensors 104 may also be configured to collect cleaning activity data during the cleaning process, which may be used to provide real-time feedback to the cleaner. The sensors 104 may transmit the activity data and cleaning activity data to either computing device 502 or output device 302.

The disinfection system 500 may also include computing device 502. The computing device 502 may be, for example, a cloud server or central controller. The computing device 502 may be configured to receive activity data from the sensors 104 and generate a contamination map from the data. The computing device 502 may also be configured to receive cleaning activity data from the sensors 104 and update the contamination map accordingly. The computing device 502 may also store any timing requirements for the setting time of disinfectants, the reflectivity of various surfaces in the room, any dose requirements, and other cleaning parameters. The computing device 502 may be configured transmit the contamination map to output device 302.

The output device 302 may display the contamination map to a user in order to aid the user in cleaning the room. The output device 302 may be, for example, an augmented reality system, a mobile computing device, or a projector that correlates hot spots in the contamination map to actual physical areas in the room. This provides a visualization of areas in the room that a user should clean. The output device 302 may also update the displayed contamination map based on cleaning activity data collected by the sensors 104.

In some embodiments, the disinfection system 500 does not include computing device 502. Rather, the functions of computing device 502 may be performed by the output device 302. In some embodiments, the disinfection system 500 may also include autonomous cleaning units, not illustrated in FIG. 5. For example, instead of providing the contamination map to an output device for viewing by a user, the contamination map may be provided to a robot, drone, or other automated cleaning system. The automated cleaning system may then clean the room according to the contamination map. The disinfection system 500 may also include other components not illustrated in FIG. 5.

Figure 6:
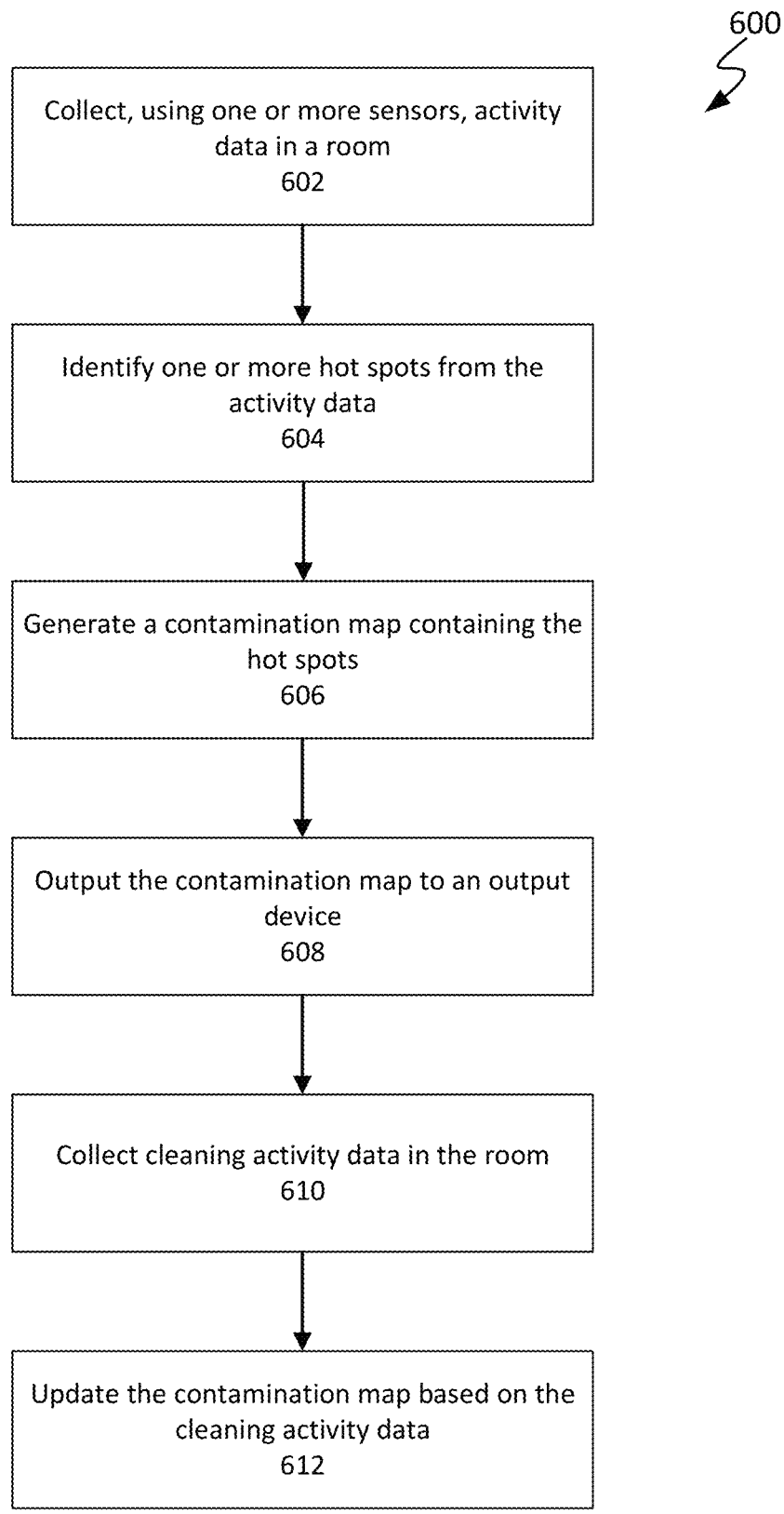
FIG. 6 is a flow diagram of a method for aiding disinfection of a room in accordance with embodiments of the present disclosure.

FIG. 6 is a flow diagram of a method 600 for aiding disinfection of a room in accordance with embodiments of the present disclosure. The method 600 may be performed by a disinfection system, such as disinfection system 500, which is used to monitor a room (e.g., a hospital room).

In block 602, one or more sensors in the disinfection system may collect activity data in the room. The activity data may include, for example, interactions between people and objects and surfaces in the room. For example, the sensors may track a location and size of a person's contact with a surface in the room, an amount of time a person has contacted the surface, movement of objects within the room, movement of liquids in the room, changes in properties of objects and surfaces in the room, and other parameters. The sensors may include at least one of an infrared sensor, a depth-sensing camera, a laser scanner, a three dimensional motion sensor, a two dimensional motion sensors, an ultraviolet sensor, a thermal imager, and a time-of-flight depth sensor.

In block 604, the disinfection system may identify one or more hot spots from the activity data. Examples of hot spots may include surfaces, areas, or objects that have been physically touched one or more times by a person, exposed to fluids, or objects that have been moved. In some embodiments, there may be a threshold of activity for an area before it is considered a hot spot. For example, there may be a minimum time that a person may occupy or touch a surface or object before it is considered a hot spot, or there may be a minimum number of contacts between a person and a surface before it is considered a hot spot. A computing device or output device in the disinfection system may receive the activity data from the sensor and identify the hot spots.

In block 606, the disinfection system may generate a contamination map containing the hot spots. The contamination map may be an image or visualization of the room that includes the hot spots indicating which areas of the room should be cleaned. A computing device or output device in the disinfection system may generate the contamination map.

In block 608, disinfection system may output the contamination map to an output device for display to a user. The output device may be, for example, an augmented reality system, a mobile computing device, or a projector. A user may utilize the contamination map to prioritize cleaning within the room.

In block 610, the one or more systems may collect cleaning activity data in the room. For example, the sensors may collect data on which hot spots have been cleaned, radiance measurements of cleaned surfaces to determine the dose applied to those surfaces, and the amount of time that a disinfectant has been applied to the surface.

In block 612, the disinfection system may update the contamination map based on the cleaning activity data. For example, hot spots that have been sufficiently cleaned may change color or disappear from the contamination map. In some embodiments, there may be a visual indication of how long a disinfectant has been allowed to set on a surface and whether that amount of time is sufficient, or the measured dose applied to a surface and whether that dose is sufficient.

FURTHER CONSIDERATIONS

The foregoing description of the embodiments of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

What is claimed is:

1. A disinfection system, comprising:
   one or more sensors configured to:
      collect activity data and cleaning activity data in a room; and
      output the activity data and the cleaning activity data; and
   an output device configured to:
      receive the activity data and the cleaning activity data from the one or more sensors;
      identify one or more hot spots based on the activity data, wherein the one or more hot spots indicate areas in the room for cleaning;
      generate a contamination map containing the one or more hot spots;
      display the contamination map to a user;
      update the contamination map based on the cleaning activity data, wherein the update comprises at least one of indicating how long a disinfectant has been set on the one or more hot spots, indicating a measured dose of the disinfectant applied to the one or more hot spots, and indicating whether the measured dose is sufficient to disinfect the one or more hot spots; and
      display the updated contamination map to the user.

2. The system of claim 1, wherein the cleaning activity data comprises at least one of radiance measurements of the one or more hot spots during cleaning and an amount of time the disinfectant has been applied to the one or more hot spots.

3. The system of claim 1, wherein the one or more sensors comprise at least one of an infrared sensor, a depth-sensing camera, a laser scanner, a three dimensional motion sensor, a two dimensional motion sensors, an ultraviolet sensor, a thermal imager, and a time-of-flight depth sensor.

4. The system of claim 1, wherein the output device comprises one of an augmented reality system, a mobile computing device, and a projector.

5. The system of claim 1, wherein the activity data comprises at least one of a location and size of a person's contact with a surface in the room, an amount of time a person has contacted the surface, movement of objects within the room, movement of liquids in the room, and changes in properties of objects and surfaces in the room.

6. A disinfection system, comprising:
   one or more sensors configured to:
      collect activity data and cleaning activity data in a room; and
      output the activity data and the cleaning activity data; and
   a computing device configured to:
      receive the activity data and the cleaning activity data from the one or more sensors;
      identify one or more hot spots based on the activity data, wherein the one or more hot spots indicate areas in the room for cleaning;
      generate a contamination map containing the one or more hot spots; and
      output the contamination map to an output device;
      update the contamination map based on the cleaning activity data, wherein the update comprises at least one of indicating how long a disinfectant has been set on the one or more hot spots, indicating a measured dose of the disinfectant applied to the one or more hot spots, and indicating whether the measured dose is sufficient to disinfect the one or more hot spots; and
      output the updated contamination map to the output device; and
   the output device, wherein the output device is configured to:
      display the contamination map and the updated contamination map to a user.

7. The system of claim 6, wherein the cleaning activity data comprises at least one of radiance measurements of the one or more hot spots during cleaning and an amount of time the disinfectant has been applied to the one or more hot spots.

8. The system of claim 6, wherein the one or more sensors comprise at least one of an infrared sensor, a depth-sensing camera, a laser scanner, a three dimensional motion sensor, a two dimensional motion sensors, an ultraviolet sensor, a thermal imager, and a time-of-flight depth sensor.

9. The system of claim 6, wherein the output device comprises one of an augmented reality system, a mobile computing device, and a projector.

10. The system of claim 6, wherein the activity data comprises at least one of a location and size of a person's contact with a surface in the room, an amount of time a person has contacted the surface, movement of objects within the room, movement of liquids in the room, and changes in properties of objects and surfaces in the room.

11. A method for aiding disinfection of a room, the method comprising:
    collecting, by one or more sensors, activity data in the room;
    identifying one or more hot spots from the activity data, wherein the one or more hot spots indicate areas in the room for cleaning;
    generating a contamination map containing the one or more hot spots;
    outputting the contamination map to an output device for viewing by a user;
    collecting, by the one or more sensors, cleaning activity data in the room as it is cleaned; and
    updating the contamination map based on the cleaning activity data, wherein the updating comprises at least one of indicating how long a disinfectant has been set on the one or more hot spots, indicating a measured dose of the disinfectant applied to the one or more hot spots, and indicating whether the measured dose is sufficient to disinfect the one or more hot spots.

12. The method of claim 11, wherein the cleaning activity data comprises at least one of radiance measurements of the one or more hot spots during cleaning and an amount of time the disinfectant has been applied to the one or more hot spots.

13. The method of claim 11, wherein the one or more sensors comprise at least one of an infrared sensor, a depth-sensing camera, a laser scanner, a three dimensional motion sensor, a two dimensional motion sensors, an ultraviolet sensor, a thermal imager, and a time-of-flight depth sensor.

14. The method of claim 11, wherein the output device comprises one of an augmented reality system, a mobile computing device, and a projector.

15. The method of claim 11, wherein the activity data comprises at least one of a location and size of a person's contact with a surface in the room, an amount of time a person has contacted the surface, movement of objects within the room, movement of liquids in the room, and changes in properties of objects and surfaces in the room.

* * * * *